United States Patent [19]

Templeton

[11] Patent Number: 4,714,445
[45] Date of Patent: Dec. 22, 1987

[54] WARMED ANIMAL TOY

[76] Inventor: Charles B. Templeton, 701 Don Mills Rd. #2600, Toronto, Canada, M3C-1R9

[21] Appl. No.: 909,587

[22] Filed: Sep. 22, 1986

[30] Foreign Application Priority Data

Sep. 27, 1985 [CA] Canada .................................. 491772

[51] Int. Cl.$^4$ .............................................. A61F 7/08
[52] U.S. Cl. ...................................... 446/74; 446/369
[58] Field of Search ........................ 446/74, 369; 5/451

[56] References Cited

U.S. PATENT DOCUMENTS

| | | | |
|---|---|---|---|
| 1,374,088 | 4/1921 | Miller | 5/451 |
| 1,558,278 | 10/1925 | Phillips | 446/74 |
| 1,896,663 | 2/1933 | Collins . | |
| 2,538,123 | 1/1951 | Price | 446/74 |
| 2,540,701 | 2/1951 | Thorpe | 446/369 |
| 2,591,379 | 4/1952 | Schradermeier | 446/74 |
| 2,647,195 | 7/1953 | Broyles . | |
| 2,913,833 | 11/1959 | Glintz . | |
| 3,542,032 | 11/1970 | Spencer, Jr. | 62/530 |
| 3,548,420 | 12/1970 | Spencer | 5/451 |
| 3,780,537 | 12/1973 | Spencer | 62/530 |
| 3,892,047 | 7/1975 | Müller-Scherak . | |
| 3,951,127 | 4/1976 | Watson et al. | 5/347 |
| 4,017,921 | 4/1977 | Hernandez | 5/347 |
| 4,073,021 | 2/1978 | Carlisle | 5/451 |
| 4,094,076 | 6/1978 | Baslow . | |
| 4,204,110 | 5/1980 | Smith et al. . | |

FOREIGN PATENT DOCUMENTS 74794  1/1947  Norway .

Primary Examiner—Victor N. Sakran
Attorney, Agent, or Firm—Riches, McKenzie & Herbert

[57] ABSTRACT

A soft, lightweight toy for a child having an animal-like appearance and feeling warm to the touch of a child. The toy comprises a thin, flexible fabric cover defining a recess. A bladder containing a fluid is removably received in the recess and adapted to lie in contact with inner surfaces of the cover so as to provide a thin layer of the fluid adjacent inner surfaces of the cover. The bladder may be removed and warmed by various means to a desired temperature. Upon insertion into the recess, heat from the bladder is transferred through the cover making the toy warm to the touch. Apart from the thin layer of fluid encapsulated in the bladder under the inner surfaces of the cover, the toy comprises low density materials.

22 Claims, 17 Drawing Figures

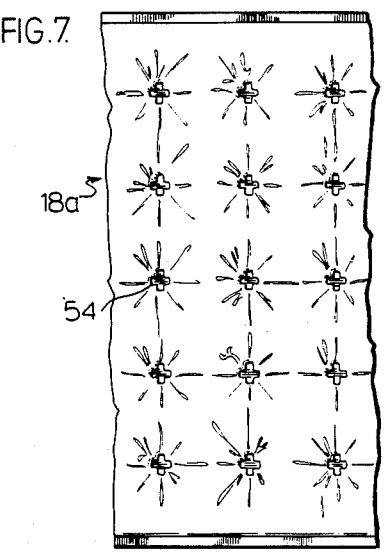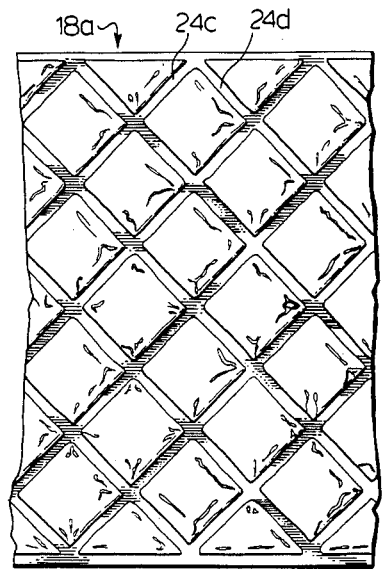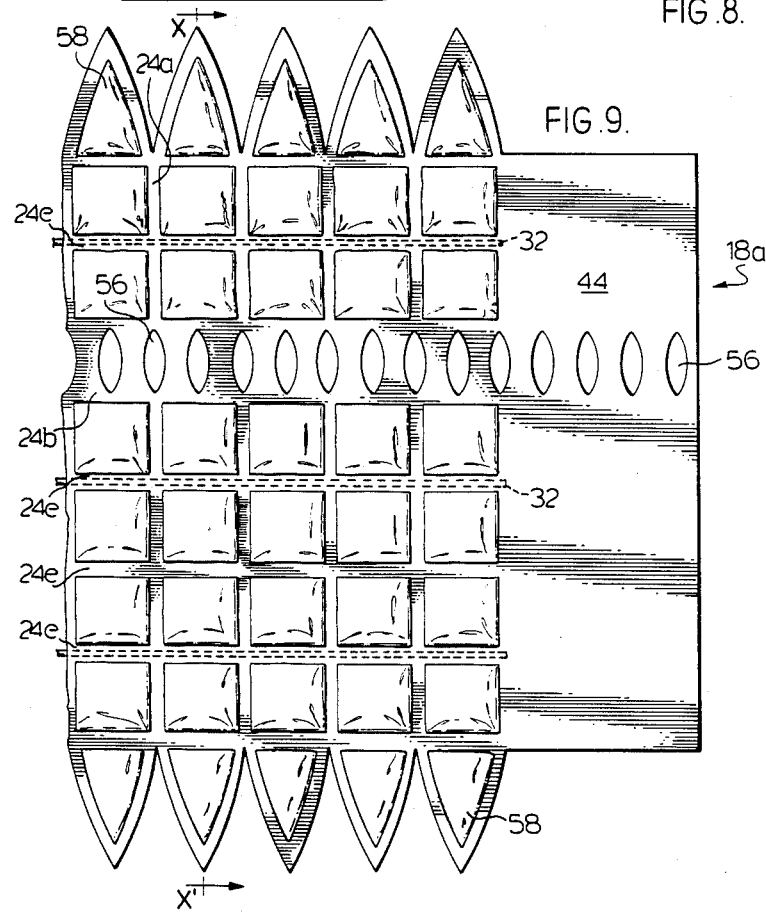

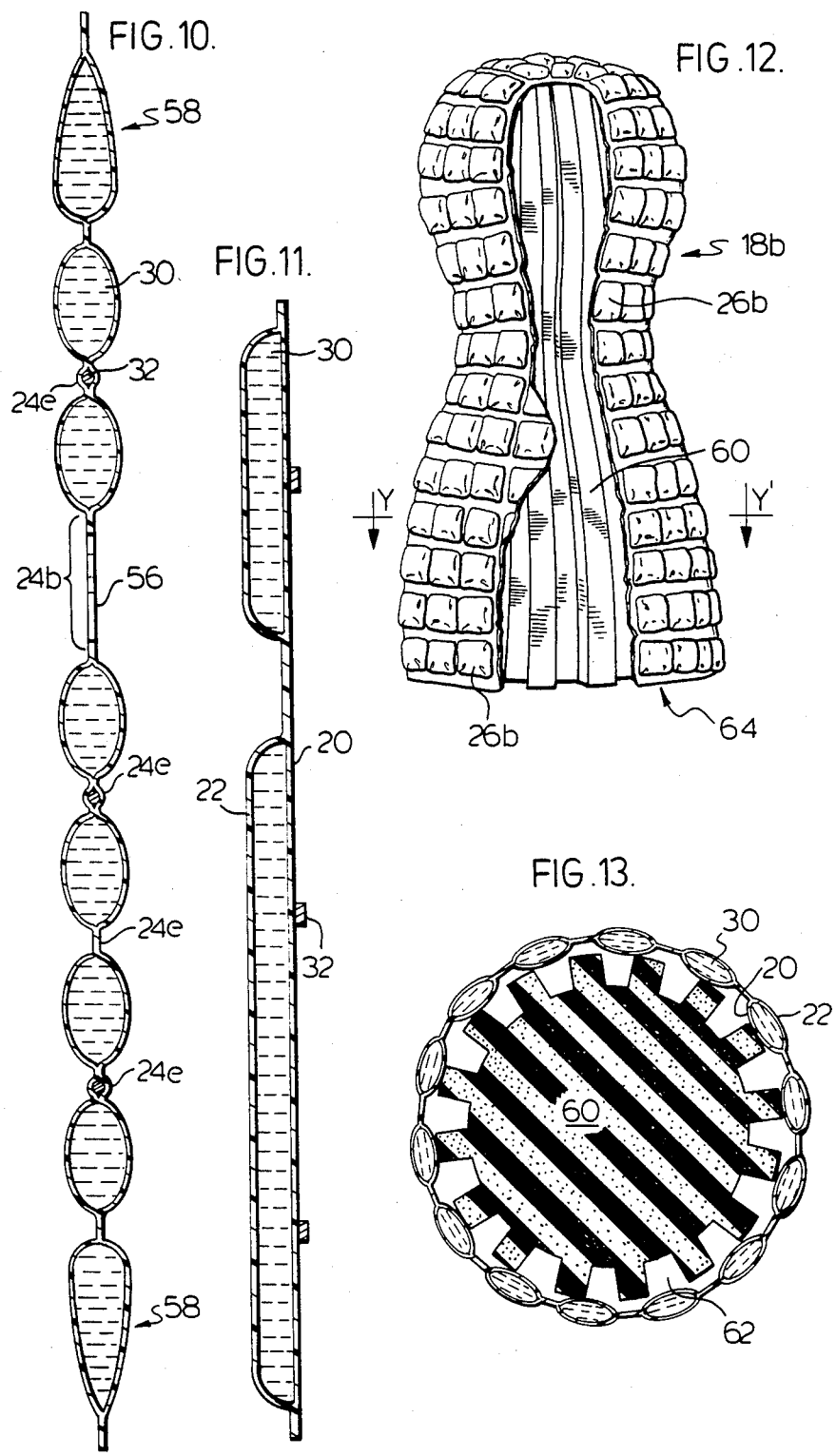

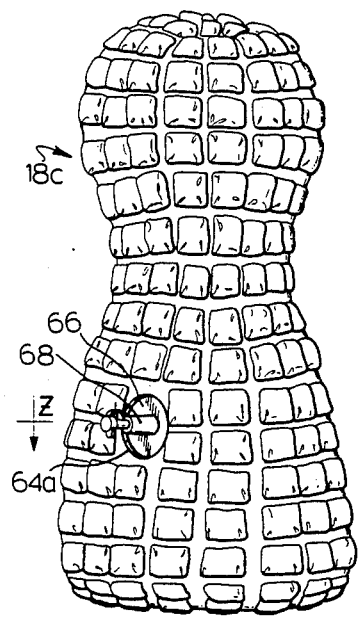
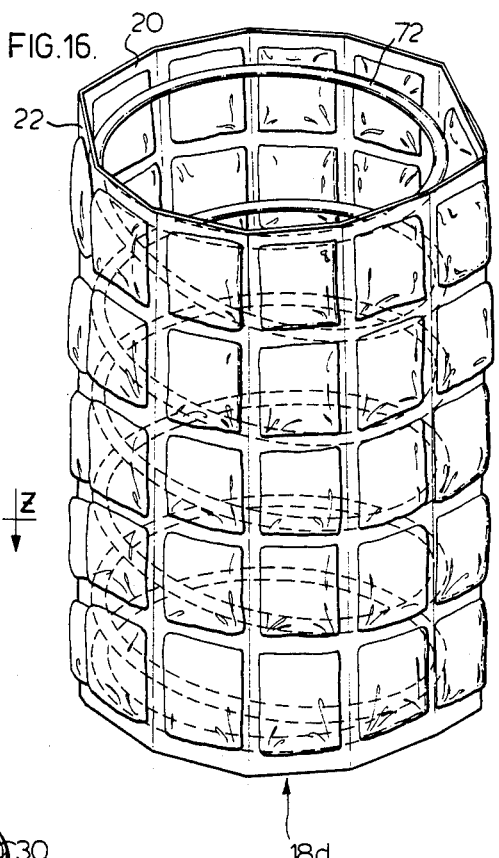
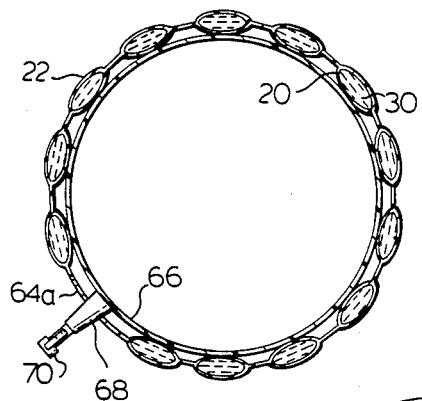
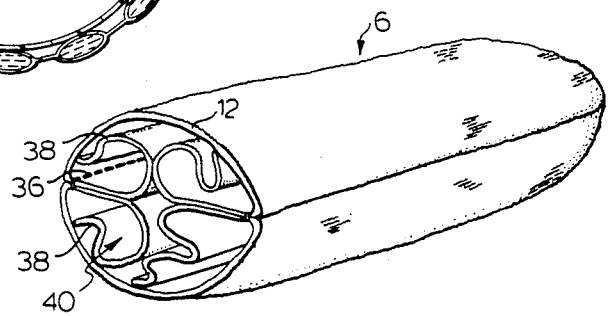

WARMED ANIMAL TOY

BACKGROUND OF THE INVENTION

This invention relates most particularly to soft animal-like or human-like toys which are warm to the touch of a child.

In the past, many attempts have been made to provide soft animal-like toys, such as stuffed teddy bears, which feel warm to the touch. Known toys which are adapted to feel warm suffer a number of disadvantages including the disadvantages of being potentially hazardous to children, too heavy, too hard or requiring complex manipulation to effect warming. For example, U.S. Pat. No. 4,204,110 to Smitt teaches an animal-like toy filled with water to be heated by an electrical heating device. The toy of Smitt suffers the disadvantages that the use of electricity has great potential for harm and that the toy when filled with water is unacceptably heavy.

SUMMARY OF THE INVENTION

Accordingly, it is an object of the present invention to at least partially overcome these disadvantages by providing a lightweight toy with a relatively thin layer of heat dissipating fluid provided closely under a thin, heat-transmitting outer cover.

Another object is to provide a lightweight toy with an internal bladder which can be removed from the toy and placed in contact with water of suitable temperature to heat or cool the material in the bladder to a desired temperature.

Another object is to provide a lightweight toy which can be heated to feel warm to the touch, yet is safe and presents no hazard to a child either in use or during the steps of warming the toy.

Another object is to provide a toy which feels warm to a child yet is soft to the feel and of a weight comparable to that of conventional stuffed animal toys.

To this end, in one of its aspects, the present invention provides a soft, lightweight toy comprising flexible, heat-transmitting cover means defining an enclosed recess therein, flexible bladder means removably received in the recess, the bladder means having an outer wall and an inner wall and retaining therebetween a first material preferably having a high density, high specific heat and high thermal conductivity, the outer wall located adjacent inside surfaces of the cover means, the inner and outer walls spaced relatively small distances apart so that the bladder means provides a relatively thin layer of said first material underlying the cover means over substantial portions of inside surfaces of the cover means yet with the layer of said first material having sufficient thickness to provide a substantial heat reservoir or sink.

In another aspect the present invention provides a soft, lightweight toy comprising lightweight, resiliently deformable core means, underlayer forming means substantially surrounding the core means, removable flexible cover means enclosing the underlayer means and core means, wherein the underlayer means is sandwiched between the core means and cover means in close contact with inside surfaces of the cover means and provides thereunder a relatively thin layer of a first material comprising a fluid or gel with high density, high specific heat and high thermal conductivity, wherein contact of outside surfaces of the cover means by a user will impart to the user a feeling of the toy having a temperature comparable to the temperature of the first material, the underlayer means is removable from the cover means for heating or cooling to a desired temperature and is reinsertable into the cover means.

In a further aspect the present invention provides a lightweight personal warming or cooling device comprising heat-transmitting closure forming cover means, underlayer means comprising a layer of first material of relatively high density, high specific heat and high thermal conductivity underlying the cover means immediately adjacent to interior surfaces of the cover means, the layer having sufficient thickness to act as a substantial heat reservoir or sink, the underlayer means comprising a relatively small proportion of the volume occupied by the toy with the remaining substantial balance of the volume occupied by relatively low density materials, the underlayer means being removable from and insertable into said cover means through access opening means in the cover means.

The present invention in its preferred aspects provides a soft, lightweight toy having the appearance of an animal or human which is designed to be hugged and carried by a child. The toy preferably has a soft, thin outer covering of a plush fabric. Closely underlying the outer covering, there is provided a removable layer of warmed heat retaining material such as water or another fluid or gel warmed to feel warm to the touch. Relatively dense materials including non-toxic fluids such as water and glycerol and similar gels may advantageously serve as the material to be warmed. Such materials preferably have relatively high specific heat representing their ability to absorb substantial quantities of heat per change in temperature per mass and relatively high thermal conductivity representing their ability to transfer heat. To provide sufficient mass of the warmed materials at locations under the outer covering of the toy so that the toy feels warm for an acceptable period of time yet does not unduly increase the weight of the resultant toy, the warmed materials are provided as a layer underlying the outer covering. Preferably aside from the layer of warmed material, the toy will be made of relatively lightweight, low density materials.

The toy preferably has a flexible outer cover enclosing a recess therein. An access opening provides entry to the recess. A sealed bladder containing the high density material to be warmed is able to be inserted into the recess and removed therefrom. The bladder is, when inserted, to assume a configuration of a thin underlayer underlying the inner surfaces of the cover in contact therewith. The blaadder may be pre-formed to assume such a configuration by means including compressible spring means and collapsible foamed plastic or air inflated cores to be received centrally in the recess and sandwich the bladder between the core and the cover. To reduce the weight of the overall toy the bladder may preferably have an inherent bias to urge itself outward into the cover with the substantial remainder of the recess occupied by a relatively low density materials, preferably air.

The bladder containing the high density material may be removed from the toy and heated to a desired temperature as by placing the bladder in contact with warmed water. The bladder and warmed material may then be inserted into the toy to present the feeling of the toy being warm until the heat in the bladder has been dissipated.

BRIEF DESCRIPTION OF THE DRAWINGS

Further objects and advantages of the present invention appear from the following description taken together with the accompanying drawings in which:

FIG.1 is a cross-sectional view through the drawings of FIG. 1 along line II–II', FIGS. 5 to 9 show schematic representations of bladders depicting a number of different constructions therefore, FIG. 10 is a cross-section through the bladder of FIG. 9 along line X-X', FIG. 11 shows a cross-section through a modified form of the bladder of FIG. 3 along line V—V', FIG. 12 is a partially cut away pictorial view of another embodiment of a bladder, FIG. 13 is a cross-sectional view of the bladder of FIG. 12 along line Y-Y', FIG. 14 is a pictorial view of another embodiment of a bladder, FIG. 15 is a cross-sectional view of the bladder of FIG. 14 along line Z-Z', FIG. 16 shows a pictorial view of another embodiment of a bladder, and FIG. 17 shows a pictorial sectional view through one arm of the toy of FIG. 1.

DETAILED DESCRIPTION OF THE DRAWINGS

Figure 1:
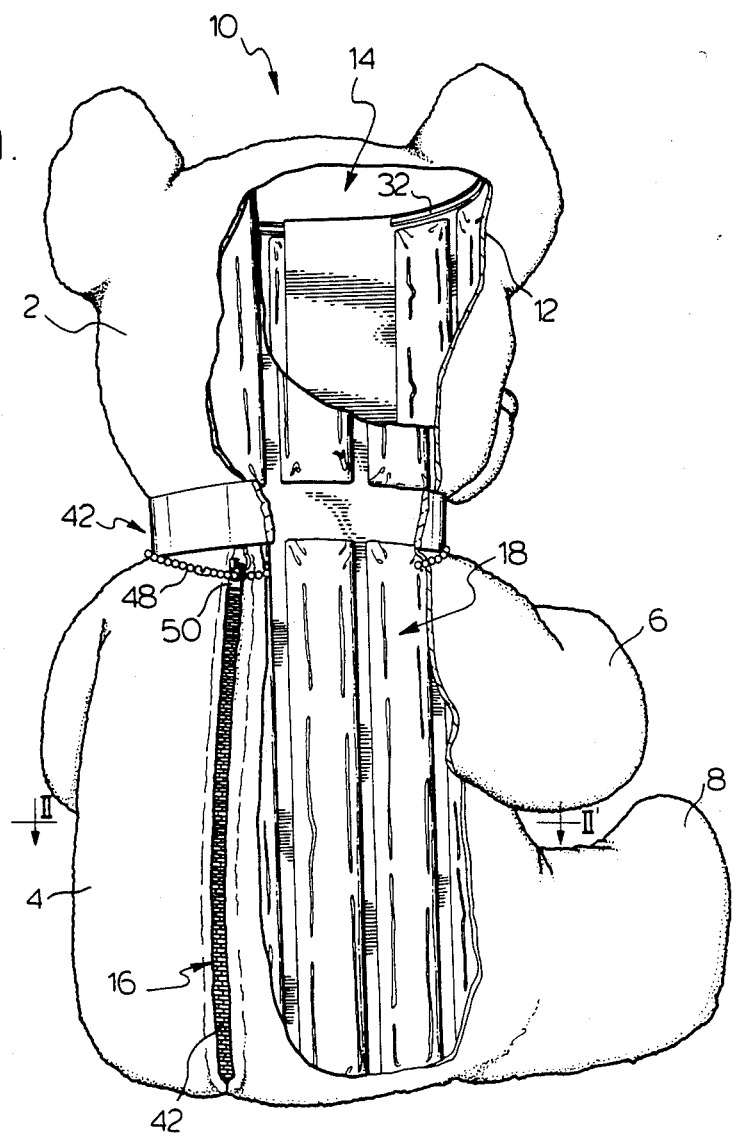
FIG. 1 is a partially cut away pictorial view of a toy in accordance with the present invention.

Reference is made first to FIG. 1 which shows a toy generally indicated 10. Toy 10 has an outer cover 12 giving the toy the appearance of a bear-like animal with head 2, body 4, arms 6 and legs 8. Cover 12 defines an enclosed central recess 14 within head 2 and body 4. An access opening 16 through cover 12 provides access to recess 14.

Figure 2:
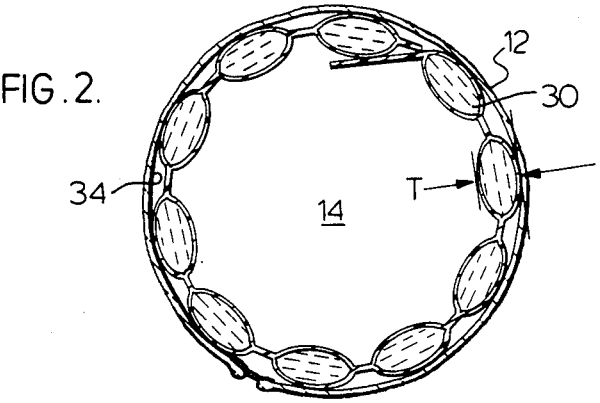
Figure 3:
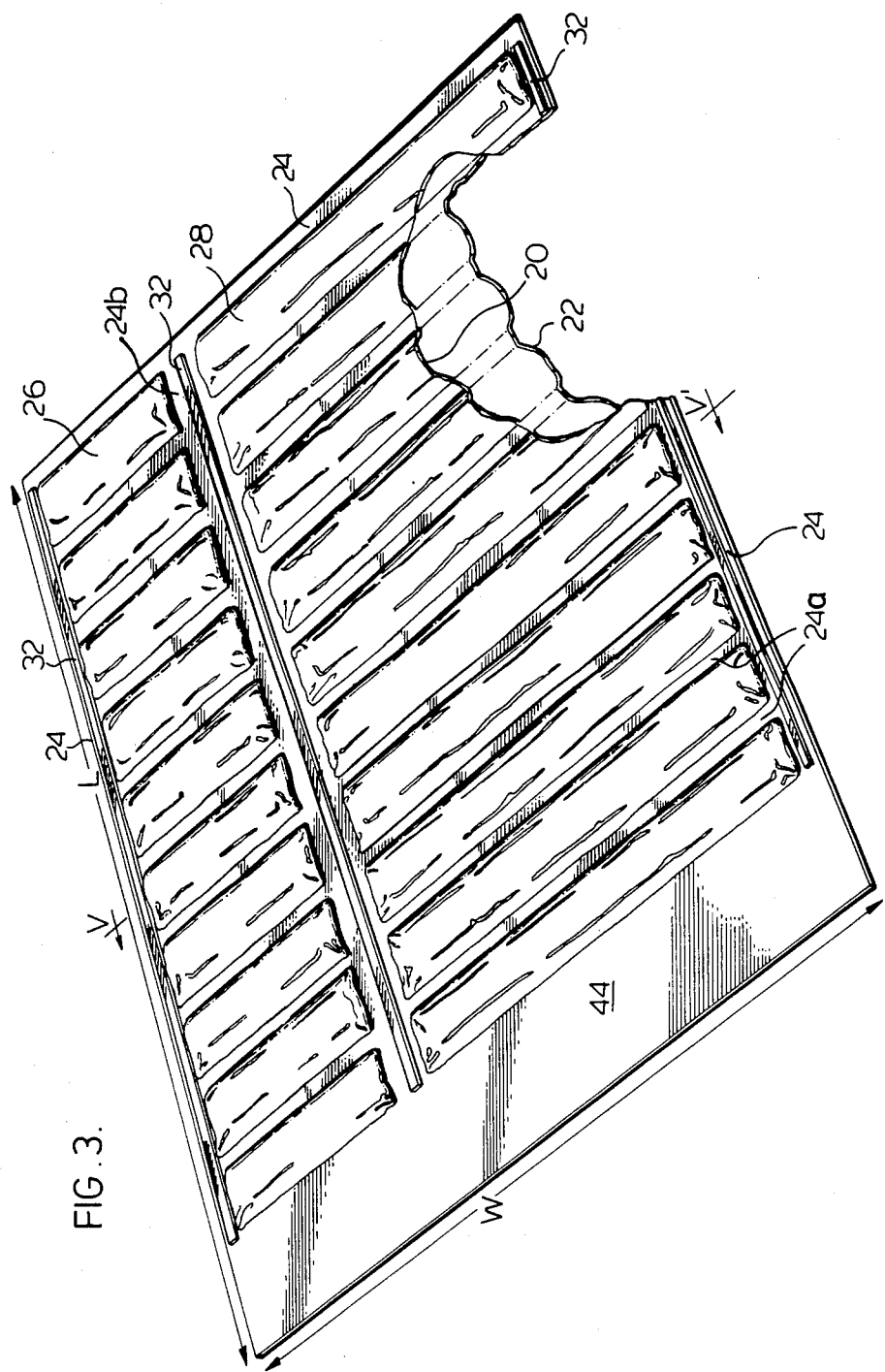
FIG. 3 shows the bladder shown in the toy of FIG. 1, uncoiled in plan view.

A bladder 18 is disposed within recess 14. Bladder 18 is best seen in FIG. 3 comprising two planar sheets 20 and 22 of fluid impermeable plastic sealed together one on top of the other along seal joints indicated generally as 24 to define a plurality of individual sealed compartments 26 and 28 filled with fluid 30. By the relatively close spacing of seal joints 24 and particularly parallel joints 24a, bladder 18 has a sheet-like configuration with a thickness indicated as "T" in FIG. 2 which is small compared to the width "W" and length "L" of the sheets. Provision of parallel seal joints 24a also assist in permitting bladder 18 to be manually rolled into a coil as seen in FIG. 4, in which coiled position the bladder can readily be inserted into cover 12 through access opening 16.

Three stays 32 best shown in FIG. 3 are coupled to bladder 18 to extend thereacross normal to seal joints 24a and thus normal to the axis about which the bladder may be coiled. Stays 32 are made of resiliently flexible, elastically deformable mataerial, preferably plastic or rubber, which permits bladder 18 to be coiled yet biases the bladder when coiled to uncoil and return to a comparatively open, flat configuration as shown in FIG. 3.

Figure 4:
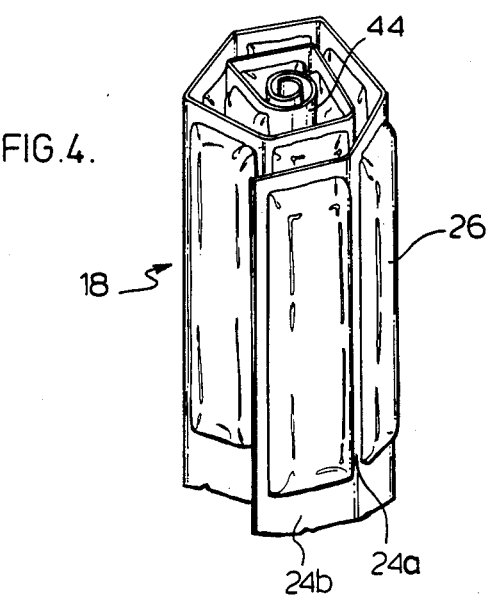
FIG. 4 shows the bladder of FIG. 3 is a fully coiled configuration.

In the toy of FIG. 1, with bladder 18 coiled as shown in FIG. 4, the bladder may readily be inserted into cover 12 through opening 16. Once inserted the bladder may be located in a desired location with the axis about which the bladder is coiled extending from head 2 to body 4 and released. Bladder 18 will uncoil under the bias of stays 32 so that the bladder, constrained by the interior surfaces of the cover, assumes a relatively uncoiled cylindrical configuration as seen in FIGS. 1 and 2 with the bladder in close contact with substantial portions of the inner surface 34 of cover 12. Bladder 18 thus in effect provides a layer of fluid 30 under cover 12 closely adjacent inner surfaces 34 of the cover.

Fluid 30 preferably has a relatively high density, relatively high specific heat and relatively high thermal conductivity. Suitable fluids 30 include water or glycerol although suitable gels may be substituted therefore.

Bladder 18 when separated from the toy may be placed into an environment which will exchange heat with the bladder to change the temperature of fluid 30 to a desired temperature. One convenient method is to place the bladder in a conventional household sink or bathtub in contact with water of desired temperature. Thus, the bladder may be cooled or warmed to a desired temperature. Bladder 18 is then dried, rolled into a coil as shown in FIG. 4 and inserted into cover 12. Warmth from bladder 18 may be felt by a child contacting the toy due to heat being transferred from the bladader through the cover. Preferably cover 12 is chosen to be heat-transmitting, as for example, with at least portions of the body 4 comprising a thin layer of material such as woven fabric which readily permits heat to pass therethrough. Advantageously soft woven fabrics including plush or velour fabrics with nap may be used to permit heat and air to pass therethrough yet to some extent retain heat and continue to feel warm once heated by the bladder.

Provided at least some portions of the cover facilitate heat transfer so that on touching the toy a child will feel the warmth of the bladder thereunder, other portions of the cover may be provided, for example with two layers of fabric having conventional stuffing therebetween which, while substantially reducing heat transfer, may be advantageous to provide a decorative pleasing appearance of the toy. Similarly, the head may have a resilient but relatively firm face piece in the head to provide a pleasing appearance albeit with a possible reduction of heat exchange ability.

In the toy shown in FIG. 1, it may be seen that bladder 18 occupies but a small proportion of the volume of recess 14 with the substantial remainder of this volume occupied by air. Movement of air inside the toy may advantageously transfer heat from the bladder to portions of the cover not in contact with the bladder, for example to the top of head 2 and bottom of body 4 as seen in FIG. 1. To enhance such air heating, cover 12 preferably is a fabric permitting some air passage therethrough. If a decorative but impermeable face plate may be provided in head 2, small air passage holes may be provided therethrough.

Arms 6 and legs 8 are preferably hollow providing air passageways therethrough to permit some passage of air therethrough whereby heat from the bladder may to some extent also be dissipated from the bladder in the recess internally through the arms and legs. A covenient method of manufacture of the arms and legs to give body thereto without the use of conventional stuffing is, as shown in FIG. 17, to sew the arm or leg with seams 36 leaving a considerable amount of excess overage 38. On turning the arm inside out for use after sewing overage 38 provides some filler to the arm and establishes air passageways 40 therethrough.

The bear-like toy 10 of FIG. 1 has a relatively large diameter neck 42 compared to the head and body to facilitate use of bladder 18 assuming a generally hollow cylindrical shape inside recess 14 as seen in FIG. 1 and yet substantially fill cover 12 urging cover 12 outwardly. Seal joint 24b is provided with a substantial width so as to eliminate fluid containing compartments in bladder 18 in the immediate vicinity of the neck 42 and permit the bladder when uncoiled to assume a somewhat hourglass shape.

Smooth, flat flap 44 may be provided on one end of bladder 18 to assist in permitting the end of the bladder carrying the flap to slide across the inner surface of the bladder when the bladder is uncoiling or is being coiled or compressed for removal from recess 14.

Zipper 46, preferably of plastic, is provided as a closure means to close opening 16. Many other closure devices such as hook and eyelete fabric fasteners sold under the VELCRO trade mark are suitable. A necklace 48 of a simple ball and chain type extends around the toy's neck. If one end of the necklace is passed through the hole in the clasp 50 for the zipper, necklace 48 on closing may effectively maintain zipper 46 in a closed position against opening by small children.

Bladder 18 is chosen to have compartments of fluid 30 of relative size and thickness so that the underlayer of fluid has sufficient mass to provide a substantial relative heat reservoir when the fluid is warmed above room temperature or a substantial relative heat sink when the fluid is cooled below room temperature. For example, when heated the fluid 30 should have sufficient heat retained therein to feel warm for a period of time. Desirable periods of time are in the range of 5 to 60 minutes, typical time periods for a child soothed by the warm toy to fall asleep. Similarly, when cooled, the fluid 30 should be able to absorb sufficient heat and thus act as a substantial heat sink to feel cool for a period of time.

The mass of the fluid is chosen to provide a desired, substantial heat reservoir or sink yet without unduly increasing the overall weight of the toy. With fluid 30 having a high density and high specific heat, a comparatively small volume of fluid may act as a reservoir to store a considerable amount of heat energy by a relatively small increase in temperature of the bladder above ambient, room temperature, for example temperature increases to 80° to 120° F. Contact of the outside surfaces of the cover by a child will impart to the child a feeling of the toy having a temperature comparable to the temperature of fluid 30 in the bladder.

The sheet of material 22 which forms the outside wall of bladder 18, to be in contact with inside surface 34 of cover 12 preferably comprises a material which will readily permit heat exchange therethrough. Preferably both sheets 20 and 22 forming the inside wall and outside wall will permit heat exhange as is advantageous when the bladder may be placed in contact with hot tap water to warm the bladder. With both the inner wall and outer wall of the bladder permitting heat transfer with the tap water, the surface area for heat exchange is increased. Soft, smooth, impermeable vinyl and other plastic materials ar suitable for the bladder, particularly those materials which can readily be sealed together. The material for sheets 20 and 22 also should be water repellant so they can easily be dried after immersion in water to heat or cool the bladder.

While bladder 18 of FIGS. 1 to 4 is manufactured from two sheets 20 and 22 as best seen in FIG. 3, in the use of preferred sheeting materials such as vinyl plastic, the two sheets are preferably fused together at the location of the seal joints. Accordingly, in FIG. 2 the two sheets are shown fused as an integral unit at seal joints.

Reference is now made to FIGS. 5 to 9 which show sections of bladders 18a similar to bladder 18 of FIG. 2 but having different configurations of seal joints to bond sheets 20 and 22 together. Each bladder when filled will have an acceptable thickness and flexibility.

Figure 5:

FIG. 5 shows bladder 18a with parallel heat seals 24a forming but single narrow compartments extending the width of the bladder.

Figure 6:
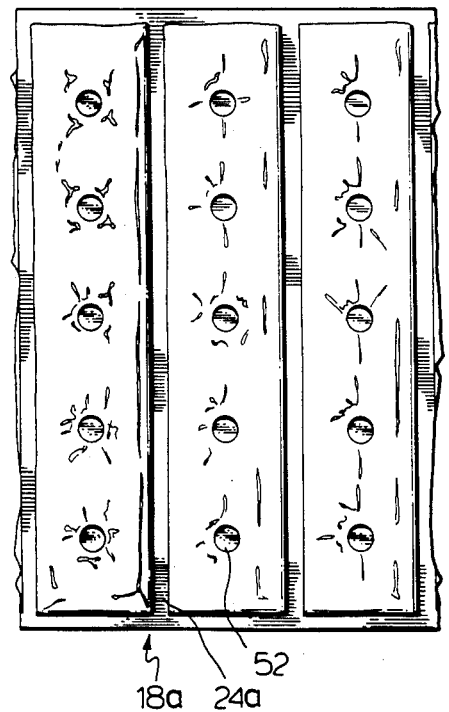

FIG. 6 shows parallel seals 24a spaced farther apart than in FIG. 5 with the sheets sealed flat together inside circles 52.

FIG. 7 shows bladder 18a as similar to the bladder of FIG. 6 with the exception that a single compartment is provided with the sheets sealed together inside the compartments by cross-shaped seal joints 54.

FIG. 8 shows the bladder with a plurality of straight seals 24c and 24d criss-crossing at an angle to be axis about which bladder 18a is to be rolled. Individual compartments are provided bordered by these seals 24c and 24d.

The bladder of FIG. 9 is shown in cross-section in FIG. 10. Parallel seal joints 24a extend the width of the bladder while parallel seal joints 24e normal to seal joints 24a reduce the width of the compartments. With seal joints 24e having an increased width, they provide a convenient location for attachment of stays 32 which may even comprise a thin resilient wire sealed between the two sheets as seen in FIG. 10. One widened seal joint 24b is shown provided with cut out portions 56 which assist in the bladder assuming an hourglass shape to conform to a narrow neck.

The bladder 18a of FIG. 10 is shown with compartments 58 coupled to the peripheral edges thereof and tapering as they extend outwardly. These compartments 58 can on uncoiling of the bladder inside the recess be urged inwardly by the cover to partially enclose the ends of the cylindrical-like configuration the bladder assumes in FIG. 1.

FIG. 11 shows a cross-section through a modified bladder which would appear in plan view similar to the bladder in FIG. 3 but in side view is seen to have sheet 20 forming the inner wall of the bladder relatively flat compared to the other sheet 22 to form the outer wall. Plastic stays 32 may readily be coupled to planar sheet 20.

Reference is now made to FIGS. 12 and 13 which shows another embodiment of a bladder 18b with a collapsible supporting core suitable as a replacement for the coilable bladder in the toy of FIG. 1. Bladder 18b may be seen to overlie and substantially enclose a core 60 of resiliently deformable foamed plastic material. Foamed core 60 advantageously is provided with grooves 62 cut therein to increase its flexibility. Bladder 18b comprises two sheets of plastic material sealed together with an inner sheet 20 closely adjacent core 60 and the outer sheet 22 to be in contact with the inside surface of cover 12. Bladder 18b has a central cavity therein enclosed by inner sheet 20 with the exception of an opening 64 at the bottom of the bladder through which compressible core 60 may be inserted and withdrawn. Inner and outer sheets 20 and 22 are sealed together as in the manner previously described to form compartments 26b and provide the bladder with an acceptable thickness. Fluid 30 is retained between the two sheets 20 and 22.

In use, bladder 18b with core 60 removed may be heated by heat exchange with tap water. After being dried, the foamed plastic core 60 is forced inside the cavity of the bladder by suitable compresion of core 60. With the bladder encompassing core 60, as a unit they may then be passed through opening 16 of cover 12. Compression of core 60 permits insertion of the bladder and core unit into the cover and its removal therefrom. Opening 16 of cover 12 may be suitably enlarged or its location changed as suitable.

FIGS. 14 and 15 shows another embodiment of a bladder 18c with an inflatable core suitable as a replacements for the coilable bladder in FIG. 1. Bladder 18c of FIG. 14 is similar to bladder 18b of FIG. 12 in that bladder 18c substantially encloses a central cavity and a supporting core is provided therein. However, the core in FIG. 14 comprises a bag 66 which can be inflated with air via tube 68 closable by closure 70. Bladder 18c is adapted for use with the cover 12 shown in FIG. 1 with an opening 16 located is in FIG. 1. Bladder 18d has a opening 64a therethrough at a location complementary to opening 16 of cover 12. Bag 66 when collapsed may be inserted inside bladder 18c via opening 64a. With bag 66 collapsed, bladder 18c containing bag 66 may be inserted into cover 12 via opening 16. With baldder 18c suitably positioned, bag 66 may be inflated via tube 68 extending through opening 64a in bladder 18d and opening 16 in cover 12 to outside the toy. On inflation of bag 66 to sandwich bladder 18c between bag 66 and cover 12, tube 68 may be sealed by closure 70 and tube 68 tucked inside cover 12 before zipping opening 16 closed. Bladder 18c may be removed by deflation of bag 66.

Rather than provide a separate bag 66, the bag could be formed integrally by inner sheet 20 of the bladder 18c being completely closed with the exception of a similar tube 68 providing communicatio therethrough.

The bladder embodiments illustrated in both FIGS. 12 and 14 have the advantage that the bladder and supporting core may be precisely shaped to conform to the particular contours of the cover, thus for example easily accomodating narrow necks or other configurations of the cover which the coiling bladder 18 of FIG. 1 could not readily accomodate.

Reference is now made to FIG. 16 which shows another embodiment of a bladder 18d suitable as a replacement for the coilable bladder of FIG. 1. In bladder 18d, inner and outer sheets 20 and 22 are formed as substantially concentric cylindrical tubes sealed to contain fluid 30 therebetween. Received within the central cavity defined by inner sheet 20 is a helical spring 72. While spring 72 may comprise an elastically deformable solid material advantageously it may comprise a hollow collapsible tube of plastic material secured to inside sheet 20 and inflatable to force bladder to assume its cylindrical shape shown after insertion of bladder 18d into cover 12. A closable air inlet tube (not shown) may be provided as a means to inflate spring 72 with such air inlet tube to extend out opening 16 for access.

Bladder 18 in FIG. 1 has been shown with individually sealed compartments 26 and 28. It is preferable that the compartments be individually sealed to approximate a uniform layer of fluid about the entire surface of the toy, and prevent fluid from tneding to settle into the lower most compartments. All the compartments could however be in communication with each other, as for example by use of a sealing configuration such as shown in FIG. 7. In such a case the bladder could be provided with a closable opening, to permit a user to place hot water inside the bladder to serve as fluid 30 which could be discarded after each use.

Whether compartments are individually sealed or not, it is desirable if the bladder compartments contain no air which may cause gurgling sounds on moving the toy.

The toy desirably should be soft and readily compressible. Preferably the bladder will not feel hard but will be formed either from elastic sheeting or with its compartments filled only to an extent to provide some resiliency. Even if the bladder compartments may be relatively firm, by suitably regulating the elasticity of stays 32 of FIG. 1, foam core 60 of FIG. 12 or the extend of inflation of bag 66 of FIG. 14, the toy may feel soft and compressible.

Preferred materials to fill the bladder and act as a heat reservoir include water, aqueous solutions, glycerol, mineral oils and various other viscous fluids or gels. The materials may preferably have relatively high densities in the range of one-half the density of water to substantially greater than the density of water. Use of glycerol with a density greater than that of water is advantageous in that the bladder will then sink in a bathtub filled with hot water to facilitate heat exchange. The specific heats and heat conductivity of hte materials preferably are comparable to or greater than that for water. The material should not stain or be toxic.

The embodiments of the bladders shown in FIGS. 5, 6 and 9 are preferably adapted to be coiled about an axis parallel to seal joints 24a. However, such bladders could be rolled about an axis normal to seal joints 24a. For example, with reference to FIG. 5, by suitable selection of the elasticity of material comprising the walls of the bladder and filling of the compartments to a desirable extent, the bladder when coiled about an axis normal to seal joint 24a may have an inherent bias to uncoil to a flat configuration in which the compartments are in a minimum stress condition.

Preferred toys in accordance with the present invention are toys having the appearance of warm-blooded animals and humans which may more readily emulate real animals and humans by feeling warm to the touch. Such animal and human toys may however by cooling of their bladders be made to feel cool to the touch, possibly to sooth a child on a hot summer evening. Toys may be specifically designed to have an appearance complementary to the toy feeling cool, for example by designing the toy to appear as a snow-man, ice-cube, or a cold blooded creature such as a fish, or a frog, dinosaur or other reptile-like life form. To provide the feel and appearance of a reptile, the cover may be made from a suitable plastic material rather than a plush cloth as is preferred for example for a bear-like toy. Rather than provide a cover, the outer wall of the bladder could provide the external surface of the toy. For example, bladder 18c shown in FIGS. 14 and 15 could itself be used as a toy without the need for a cover. With the bladder comprising a plastic material, it could present the feel of the skin of a cool reptile. The compartments could be suitably shaped to provide a desired appearance.

In cases where the outer wall of the bladder is to provide the external surface of the toy, a plastic material comprising the outer wall could have a thin layer of fabric secured thereto to provide a preferred feel to the touch.

Rather than eliminate the cover entirely, a cover could be provided with at least one opening therethrough so that the outer wall of the bladder is exposed to touch by a person feeling the toy. For example a toy appearing as a snow-man and having a plush cloth fabric cover could have an opening through the cover to expose the outer wall of the bladder as a cold chest and belly of the snowman.

Devices in accordance with the present invention can be made principally as personal heating or cooling devices for example for adults for use as a substitute to a regular hot water bottle. A bed pillow could be constructed in accordance with the present invention having, for example, a fabric outer cover and a thin bladder thereunder about a foamed core. The pillow would be lightweight and provide warmth for a considerable period of time yet feel substantially like a normal bed pillow.

In the context of providing personal heating or cooling devices, a bladder such as shown in FIGS. 5, 6 7 or 8 may by itself comprise a useful device. By making these bladders with sufficient flexibility, the bladders may be wrapped about or draped over virtually any portion of a human body to heat or cool as desired. For example, a bladder could readily be wrapped about a knee, elbow, wrist or neck. The bladder could be provided with suitable closure means such as VELCRO straps to hold the bladder in wrapped around an arm. The bladder could also be particularly configured to conform to the shape of the part of the body it is to contact.

While the present invention has been described, with reference to preferred embodiments, the invention is not so limited. Many variations and modifications will now occur to those skilled in this art. For a definition of the invention, reference is made to the following claims.

What I claim is:

1. A soft, lightweight toy comprising:
   flexible, heat-transmitting cover means defining an enclosed recess therein,
   flexible bladder means removably received in the recess,
   the bladder means having an outer wall and an inner wall and retaining therebetween a first material having a high density, high specific heat and high thermal conductivity,
   the outer wall located adjacent inside surfaces of the cover means,
   the inner and outer walls spaced relatively small distances apart so that the bladder means provides a relatively thin layer of said first material underlying the cover means over substantial portions of inside surfaces of the cover means yet with the layer of said first material having sufficient thickness to provide a substantial heat reservoir or sink.

2. A toy as claimed in claim 1 wherein the cover means and outer wall of the bladder means permit heat transmittal therethrough whereby contact of outside surfaces of the cover means by a user will impact to the user a feeling of the toy having a temperature comparable to the temperature of the first material.

3. A toy as claimed in claim 2 wherein the bladder means is removable from the cover means for placement into contact with a medium for heat exchange therewith to raise or lower the bladder means to a desired temperature before re-insertion into the cover means.

4. A toy as claimed in claim 3 wherein the inner and outer walls of the bladder means each comprise impermeable flexible plastic sheeting sealably coupled together to retain a non-toxic fluid or gel comprising the first material therebetween.

5. The bladder of claim 3 wherein,
   said inner and outer walls of the bladder means each comprises an open-ended generally cylindrical tube-like member of impermeable flexible plastic sheeting,
   the tube-like member forming the inner wall received generally co-axially within the tube-like member forming the outer wall,
   the tube-like members sealed together about their peripheries and at locations intermediate their peripheries so that with the bladder means filled with the first material the bladder means assumes a torroidal configuration with a substantial central opening therethrough, and
   the first material comprises a non-toxic fluid or gel.

6. The bladder of claim 5 wherein,
   with said bladder means received in the recess, the central opening comprises a substantial portion of the recess which is occupied by air, and
   the bladder means is biased to assume its torroidal configuration.

7. A toy as claimed in claim 4 wherein the plastic sheeting comprising the inner and outer walls are sealed together about their peripheries and at locations intermediate their peripheries spaced sufficiently closely so that with the bladder means filled with the first material, the first and second walls will only be spaced said relatively small distances.

8. A toy as claimed in claim 5 wherein the plastic sheeting comprising the inner and outer walls are sealed together to provide a plurality of individual sealed compartments filled with the fluid or gel.

9. A toy as claimed in claim 8 wherein the cover means comprises a thin layer of flexible heat transmitting woven fabric.

10. A toy as claimed in claim 7 wherein,
    the bladder means has a sheet-like configuration with the thickness between the inner and outer walls small compared to the width and length of the inner and outer walls,
    the bladder means adapted to be manually rolled into a coiled configuration, with the bladder means when coiled having an inherent bias to uncoil,
    access opening means permitting access through the cover means to the recess,
    the bladder means, recess and access opening means relatively sized and configured so that the bladder means when coiled can manually be inserted into the recess through the access opening means, located in the recess in a desired orientation and released; wherein upon release the bladder means uncoils under its bias to expand forcing the cover means outwardly to inflate the recess with the outer wall of the bladder means urged into contact with the inside surfaces of the cover means.

11. A toy as claimed in claim 10 wherein said bladder means includes elongate resiliently flexible members coupled thereto which become elastically deformed on coiling of the bladder means thereby impacting the inherent bias to the bladder means to uncoil.

12. A toy as claimed in claim 11 wherein said flexible members comprise elongate plastic members coupled to the outer walls of the bladder means to extend thereacross normal to an axis about which the bladder means is coiled.

13. A toy as claimed in claim 12 wherein the plastic sheeting comprising the inner and outer walls are sealed together to provide a plurality of individually sealed compartments filled with the fluid or gel with perimeters of the compartments arranged to facilitate coiling of the bladder means.

14. A toy as claimed in claim 13 wherein said compartments are narrow and elongate entending substantially normal to an axis about which the bladder means is coiled.

15. A toy as claimed in claim 8 wherein the compartments have a thickness sufficient to provide a substantial mass of the first material to act as a heat reservoir or sink yet provide the toy with substantially less mass than if the recess were filled with the first material.

16. A toy as claimed in claim 1 wherein the bladder means when received in the recess expands the cover means outwardly with the bladder means lying closely adjacent inner surfaces of the cover means and substantial central portions of the recess occupied by air.

17. A toy as claimed in claim 16 wherein
the cover means comprises a soft-flexible fabric material configured to have an animal-like or humanoid appearance, and
the inner and outer walls comprise plastic sheeting.

18. The toy as claimed in claim 1 wherein said first material has a density, specific heat and thermal conductivity equal to or greater than that of water.

19. The toy as claimed in claim 1 wherein said first material is selected from the group consisting of water, glycerol and mixture thereof.

20. A soft, lightweight toy comprising:
lightweight, resiliently deformable core means,
underlayer forming means substantially surrounding the core means,
removable flexible cover means enclosing the underlayer means and core means,
wherein the underlayer means is sandwiched between the core means and cover means in close contact with inside surfaces of the cover means and provides thereunder a relatively thin layer of a first material comprising a fluid or gel with high density, high specific heat and high thermal conductivity,
wherein contact of outside surfaces of the cover means by a user will impart to the user a feeling of the toy having a temperature comparable to the temperature of the first material,
the underlayer means is removable from the cover means for heating or cooling to a desired temperature and is reinsertable into the cover means.

21. A soft, ligthweight toy comprising:
flexible, heat-transmitting cover means defining an enclosed recess therein,
flexible bladder means removably received in the recess,
the bladder means having outer wall means and inner wall means and retaining therebetween a liquid or gel,
the outer wall means located adjacent inside surfaces of the cover means,
the inner and outer wall means spaced relatively small distances apart so that the bladder means provides a relatively thin layer of said fluid or gel underlying the cover means over portions of inside surfaces of the cover means,
the cover means and outer wall means of the bladder means permitting heat transmittal therethrough whereby contact of outside surfaces of the cover means by a user will impart to the user a feeling of the toy having a temperature comparable to the temperature of the fluid or gel.

22. A toy as claimed in claim 21 wherein said bladder means is biased outwardly into contact with said cover means.

* * * * *